United States Patent [19]

Brüning et al.

[11] Patent Number: 4,647,662
[45] Date of Patent: Mar. 3, 1987

[54] UNSYMMETRICAL DIHYDRODITHIAZINES, AND THEIR USE AS FRAGRANCES AND FLAVORINGS

[75] Inventors: Jürgen Brüning; Roland Emberger; Rudolf Hopp; Manfred Köpsel; Theodor Sand, all of Holzminden; Peter Werkhoff, Hoexter, all of Fed. Rep. of Germany

[73] Assignee: Haarmann & Reimer GmbH, Holzminden, Fed. Rep. of Germany

[21] Appl. No.: 810,438

[22] Filed: Dec. 18, 1985

[30] Foreign Application Priority Data

Dec. 22, 1984 [DE] Fed. Rep. of Germany ....... 3447209

[51] Int. Cl.$^4$ .................. C07D 285/00; A23L 2/26; A61K 7/46; C11B 9/00
[52] U.S. Cl. .................. 544/5; 252/522 R; 426/535
[58] Field of Search ........... 544/5; 252/522 R; 426/535

[56] References Cited

U.S. PATENT DOCUMENTS

| | | | |
|---|---|---|---|
| 1,990,963 | 2/1935 | Teppema | 544/5 |
| 2,273,664 | 2/1942 | Searle | 544/5 |
| 2,610,182 | 9/1952 | McDermott | 544/5 |
| 3,650,771 | 3/1972 | Wiener | 544/5 |
| 3,966,988 | 6/1976 | Wilson et al. | 544/5 |
| 4,228,278 | 10/1980 | Shu et al. | 544/5 |

FOREIGN PATENT DOCUMENTS 953519   3/1964   United Kingdom ................. 544/5

Primary Examiner—John M. Ford
Attorney, Agent, or Firm—Sprung, Horn, Kramer & Woods

[57] ABSTRACT

Unsymmetrical dihydrodithiazines of the formula

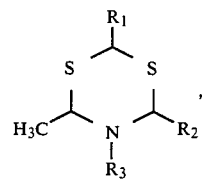

in which one of the substituents $R_1$ and $R_2$ represent a $C_3$–$C_5$-alkyl group while the other is a methyl group and $R_3$ represents a hydrogen atom, or $R_1$ represents a methyl group and $R_2$ and $R_3$ together form a $C_3$–$C_4$-alkylene radical, a process for their preparation and their use as fragrances and flavorings.

7 Claims, No Drawings

UNSYMMETRICAL DIHYDRODITHIAZINES, AND THEIR USE AS FRAGRANCES AND FLAVORINGS

The invention relates to new, unsymmetrical monocyclic or bicyclic dihydrodithiazines, a process for their preparation and their use as fragrances and flavourings.

Dihydrodithiazines, and their use as fragrances and flavourings, are known. In the British Patent Specification No. 1,364,747 the use of symmetrical dihydrodithiazines is described in general terms, while the use of symmetrical 2,4,6-triisobutyldihydro-1,3,5-dithiazine as an odorous substance and flavouring is described specifically in U.S. Patent Specification Nos. 4,200,741, 4,200,742 and 4,228,278. In practice, however, the strength and character of the aroma of these known dihydrodithiazines are still not satisfactory.

It has been found, surprisingly, that certain unsymmetrical dihydrodithiazines possess a substantially stronger aroma and that, above all, the desired note of roasting and nuts is substantially more strongly pronounced in their aroma character. Nor, in contrast with the known dihydrodithiazines, does any greasy note, which is undesirable in nutty aromas, manifest itself in the case of the unsymmetrical dihydrodithiazines.

The invention therefore relates to new, unsymmetrical monocyclic or bicyclic dihydrodithiazines of the formula

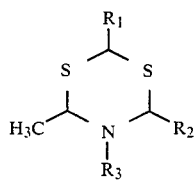

in which in each case either of the substituents $R_1$ and $R_2$ represents a $C_3$–$C_5$-alkyl group, while the other substituent is a methyl group, and $R_3$ represents a hydrogen atom, or $R_1$ represents a methyl group and $R_2$ and $R_3$ together form a $C_3$–$C_4$-alkylene radical.

Suitable $C_3$–$C_5$-alkyl radicals are, above all, the n-propyl, isopropyl, n-butyl, isobutyl, 2-butyl, n-pentyl and isopentyl radicals. Suitable $C_3$–$C_4$-alkylene radicals are above all the propylene-1,3 and the butylene-1,4 radical.

The following may be mentioned as preferred representatives of the unsymmetrical dihydrodithiazines according to the invention: 4,6-dimethyl-2-isopropyldihydro-1,3,5-dithiazine, 2,4-dimethyl-6-isopropyldihydro-1,3,5-dithiazine, 4,6-dimethyl-2-isobutyldihydro-1,3,5-dithiazine, 2,4-dimethyl-6-isobutyldihydro-1,3,5-dithiazine, 4,6-dimethyl-2-(2-butyl)dihydro-1,3,5-dithiazine, 2,4-dimethyl-6-(2-butyl)dihydro-1,3,5-dithiazine, 4,6-dimethyl-2-n-propyldihydro-1,3,5-dithiazine, 2,4-dimethyl-6-n-propyldihydro-1,3,5-dithiazine and 2,4-dimethyltetrahydropyrrolo[2.1-d]-[1,3,5]dithiazine.

The invention also relates to a process for the preparation of the unsymmetrical dihydrodithiazines of the formula (I); the process is characterised in that the monocyclic compounds are prepared by reacting a mixture of acetaldehyde and a $C_4$–$C_6$-alkanal with ammonia, and reacting the product of the reaction with hydrogen sulphide. The bicyclic compounds are prepared by reacting acetaldehyde with 1-pyrroline or 2,3,4,5-tetrahydropyridine and reacting the product of the reaction with hydrogen sulphide.

In addition, the invention relates to the use of the unsymmetrical dihydrodithiazines of the formula (I) as fragrances and flavourings.

The preparation of the monocyclic, unsymmetrical dihydrodithiazines can, in principle, be effected by the process already described by Wöhler and Liebig in Ann. 61, 1 (1847) for the preparation of thialdine (2,4,6-trimethyldihydro-1,3,5-dithiazine). In analogy with this process, a 2.5-molar to 4-molar excess relative to the aldehyde groups, of concentrated, aqueous ammonia is added at 0° to 20° C. to a mixture of acetaldehyde and a $C_4$–$C_6$-alkanal in which the two components are present in a molar ratio of 2.2 to 1.8:1, preferably 2:1. After stirring at room temperature for 0.5 to 1 hour, hydrogen sulphide is passed into the reaction mixture until saturation is reached. The reaction mixture is then kept at room temperature for 12 to 24 hours. After working up in the customary manner and fractional distillation, a mixture of the isomeric 2,4-dimethyl-6-$C_3$-$C_5$-alkyl-dihydro-1,3,5-dithiazine and 4,6-dimethyl-2-$C_3$-$C_5$-alkyl-dihydro-1,3,5-dithiazine is obtained. The mixture of isomers can be separated into the individual components by customary processes of separation, for example, preparative column chromatography over silica gel. However, since the mixtures of isomers only differ inconsiderably in their sensory properties from the sensory properties of the isolated isomers, it is generally possible to dispense with separating the isomers and to use the mixture of isomers as such as a fragrance and/or flavouring.

Bicyclic unsymmetrical dihydrodithiazines of formula (I) are prepared by adding an etherial solution of 1-pyrroline or 3,4,5,6-tetrahydropyridine dropwise to acetaldehyde at room temperature. The molar ratio of acetaldehyde to 1-pyrroline or 3,4,5,6-tetrahydropyridine is 1.8 to 2.2:1, preferably 2:1. The reaction mixture is saturated with hydrogen sulphide at a temperature of 0° to 20° C., and is then kept at room temperature for 12 to 24 hours.

The unsymmetrical dihydrodithiazines, according to the invention, of the formula (I) are valuable fragrances and flavourings which, on account of their nutty odour and taste, are used to alter, to improve and to intensify the character of the fragrance and flavouring compositions. When used as a fragrance, the compounds according to the invention are employed in combination with other fragrances which are in themselves known (Arctander, Perfume and flavor chemicals, Montclair, N.J. (USA), 1969) and essential oils (Arctander, Perfume and flavor materials of natural origin, Elisabeth, N.J. (USA), 1960), and afford perfume bases and fragrance compositions which have highly expressive notes and which are excellently suitable for perfuming finished products in the aerosol, washing agent and industrial chemical sector, but particularly the fine perfumery or cosmetic sector, for example for detergents, hair care pro-ducts, foam baths, bathsalts, washing-up liquids, washing powders, soaps, anti-perspirants, powders, creams, shaving lotions, after-shave lotions, air-fresheners, w.c. cleansers, room sprays, antiperspirant sprays, deodorant sprays, body sprays, insecticidal sprays and sunscreen agents.

The preparation of the perfume compositions and perfumed products is effected in a customary manner, for example by combining the components. Furthermore, the compounds according to the invention are valuable flavourings which are distinguished by very low flavour threshold values.

Thus in aqueous 0.5% strength sodium chloride solution, the threshold of recognition is between 0.5 and $5\times10^{-3}$ ppm. At and above the threshold of recognition the description of the taste of some exemplary mixtures or substances is as follows:

Mixture A (mixture of 4,6-dimethyl-2-isopropyldihydro-1,3,5-dithiazine and 2,4-dimethyl-6-isopropyldihydro-1,3,5-dithiazine, prepared in accordance with Example 4): ground nuts, cocoa, roasted note.

Mixture B (mixture of 4,6-dimethyl-2-isobutyldihydro-1,3,5-dithiazine and 2,4-dimethyl-6-isobutyldihydro-1,3,5-dithiazine, prepared in accordance with Example 1): ground nuts, hazel nuts, roasted note, meat.

Mixture C (mixture of 4,6-dimethyl-2-(2-butyl)dihydro-1,3,5-dithiazine and 2,4-dimethyl-6-(2-butyl)dihydro-1,3,5-dithiazine, prepared in accordance with Example 2): ground nuts, roasted note and fatty.

Substance D (2,4-dimethyltetrahydropyrrolo [2.1-d]-[1,3,5]-dithiazine): ground nuts, onions and roasted note.

In addition to their specific characterisation in the direction of hazelnuts or groundnuts in appropriate aroma compositions, the compounds according to the invention have a particularly rounding-off effect and rather impart naturalness in all non-nut types.

The aroma compositions prepared using the compounds according to the invention can be employed in the whole field of provisions and fine foods, oral hygiene and animal feed. They are particularly suitable for fondant compositions, nougat compositions, fatty compositions, margarine, edible oil, cake flour, biscuit compositions, bread and confectionery, extruded products, milk products, sour milk products, beverages, icecream, rubber, oral hygiene products, tobacco products, ready-cooked meals, meat and sausage products, soups, sauces, tinned vegetables, spirits, vegetable and microbial proteins and all types of industrially manufactured animal feed. The dihydrodithiazines according to the invention are used in amounts of $0.5\times10^{-3}$ ppm to 1%, preferably $1\times10^{-3}$ ppm to 100 ppm, relative to the foodstuffs ready for consumption.

EXAMPLE 1

95.2 g (1.93 mol) of concentrated aqueous ammonia are added at 5° C. to a mixture of 48.1 g (1.1 mol) of acetaldehyde and 47 g (0.55 mol) of isovaleraldehyde. After the ammonia has been added, the mixture is stirred at room temperature for half an hour, and hydrogen sulphide is then passed in for 3 hours until saturation is reached. The precipitate which has been deposited is dissolved by adding 150 ml of water, and the reaction mixture is kept at room temperature for 15 hours.

The mixture is worked up by separating off the organic phase, extracting the aqueous phase with cyclohexane and combining the cyclohexane phase with the organic phase. The organic phase is washed until it is neutral, dried and freed from solvent in vacuo. The residue is subjected to fractional distillation. The fraction passing over between 104° and 115° C. at 2.5 mbar contains the desired mixture of the two dimethylisobutyldihydrodithiazines. Part of this mixture is immediately used as an additive for an aroma composition.

The remainder is separated into the pure components 4,6-dimethyl-2-isobutyldihydro-1,3,5-dithiazine and 2,4-dimethyl-6-isobutyldihydro-1,3,5-dithiazine by chromatographic separation over silica gel 60, using an 80:20 cyclohexane/ethyl acetate solvent mixture. The pure components were characterised by their mass-spectra.

Mass-spectrum of 4,6-dimethyl-2-isobutyldihydro-1,3,5-dithiazine: 44(100); 71 (34); 70 (27); 41 (27); 60 (26); 43 (25); 45 (23); 59 (21).

Mass-spectrum of 2,4-dimethyl-6-isobutyldihydro-1,3,5-dithiazine: 43 (100); 44 (83); 60 (69); 86 (67); 59 (61); 70 (56); 41 (51); 45 (46).

EXAMPLE 2

63 g (1.43 mol) of acetaldehyde, 61.6 g (0.71 mol) of 2-methylbutyraldehyde and 124 g (2.5 mol) of concentrated aqueous ammonia are reacted as described in Example 1.

In the fractional distillation the mixture of isomers passes over between 72° and 135° C. at 3 mbar. Part of this mixture is used immediately as an additive for an aroma composition.

The remainder is separated into the pure components, 4,6-dimethyl-2-(2-butyl)-dihydro-1,3,5-dithiazine and 2,4-dimethyl-6-(2-butyl)-dihydro-1,3,5-dithiazine, by column chromatography. The pure components were characterised by their mass-spectra.

Mass-spectrum of 4,6-dimethyl-2-(2-butyl)-dihydro-1,3,5-dithiazine: 44(100); 71 (56); 70 (43); 205 (32); 103 (31); 41 (14); 56 (11); 45 (11).

Mass-spectrum of 2,4-dimethyl-6-(2-butyl)-dihydro-1,3,5-dithiazine: 86 (100); 44 (82); 205 (50); 112 (37); 84 (29); 60 (27); 41 (24); 145 (24).

EXAMPLE 3

48.1 g (1.1 mol) of acetaldehyde, 40 g (0.55 mol) of butyraldehyde and 95.2 g (1.93 mol) of concentrated aqueous ammonia are reacted as described in Example 1.

In the fractional distillation, a mixture of the two isomeric dimethyl-n-propyldihydrodithiazines passes over between 55 and 120° C. at 2.5 mbar. Part of this mixture is used immediately as an additive for an aroma composition.

The remainder is separated into its two components, 4,6-dimethyl-2-n-propyldihydro-1,3,5-dithiazine and 2,4-dimethyl-6-n-propyl-dihydro-1,3,5-dithiazine, by column chromatography.

The pure components were characterised by their mass-spectra.

Mass-spectrum of 4,6-d:methyl-2-n-propyldihydro-1,3,5-dithiazine: 44(100); 71 (29); 70 (23); 191 (12); 103 (12); 60 (11); 56 (11); 45 (11).

Mass-spectrum of 2,4-dimethyl-6-n-propyl-dihydro-1,3,5-dithiazine: 44 (100); 72 (92); 98 (51); 70 (40); 60 (31); 191 (30) 59 (27); 27 (25).

EXAMPLE 4

48,1 g (1.1 mol) of acetaldehyde, 40 g (0.55 mol) of 2-methyl-propionaldehyde and 95.2 g (1.93 mol) of concentrated aqueous ammonia are reacted as described in Example 1.

In the fractional distillation, a mixture of the two isomeric dimethyl-isopropyl-dihydrodithiazines passes over at 64° to 87° C. at 1.7 mbar. Part of this mixture is used immediately as an additive for an aroma composition.

The remainder is separated into its two components, 4,6-dimethyl-2-isopropyl-dihydro-1,3,5-dithiazine and 2,4-dimethyl-6-isopropyl-dihydro-1,3,5-dithiazine, by column chromatography over silica gel 60.

The pure components were characterised by their mass-spectra.

Mass-spectrum of 4,6-dimethyl-2-isopropyl-dihydro-1,3,5-dithiazine: 44 (100); 71 (38); 70 (29); 191 (27); 103 (19); 56 (8); 55 (8); 45 (7).

Mass-spectrum of 2,4-dimethyl-6-isopropyl-dihydro-1,3,5-dithiazine: 44 (100); 72 (93); 191 (54); 98 (26); 55 (24); 84 (23); 60 (20); 99 (19).

EXAMPLE 5

44 g (1 mol) of acetaldehyde are added dropwise to a solution of 34.5 g (0.5 mol) of 1-pyrroline in 150 ml of ether. Hydrogen sulphide is then passed into the reaction mixture, while the latter is cooled with ice, until saturation is reached. After 10 g of magnesium sulphate have been added, the reaction mixture is kept at room temperature for 15 hours. When the ether has been removed by distillation, the residue is fractionally distilled. 43 g of 2,4-dimethyltetrahydropyrrolo[2.1-d]-[1,3,5]-dithiazine (boiling point at 6 mbar: 105° C.) are obtained.

EXAMPLE 6

An aroma composition A having a hazelnut aroma is prepared by mixing the following ingredients:

| | | |
|---|---|---|
| vanillin | | 30 |
| benzaldehyde | | 10 |
| furfural | | 5 |
| 2-ethyl-3,4(3,6)-dimethylpyrazine | | 5 |
| 2-methyl-3-ethylpyrazine | | 5 |
| resorcinol dimethylether | | 50 |
| propylene glycol | | 895 |
| | parts by weight | 1,000 |

An aroma composition B is prepared by adding to A 10 parts by weight of the mixture of isomers 2,4(4,6)-dimethyl-6(2)-isopropyldihydro-1,3,5-dithiazine, obtained in accordance with Example 4.

An aroma composition C is prepared by adding to A 5 parts by weight of the mixture of isomers 2,4(4,6)-dimethyl-6(2)-isobutyldihydro-1,3,5-dithiazine, obtained by Example 1.

An aroma composition D is prepared by adding to A 5 parts by weight of the mixture of isomers 2,4(4,6)-dimethyl-6(2)-(2-butyl)-dihydro-1,3,5-dithiazine, obtained in accordance with Example 2.

An aroma composition E is prepared by adding to A 10 parts by weight of 2,4-dimethyltetrahydropyrrolo-[2.1-d]-[1,3,5]dithiazine, obtained in accordance with Example 5.

The compositions A to E are each added in a dosage of 10 ppm to a solution of 5% of sucrose in water. A comparison of the flavour of B, C, D and E against A gives the following results:

B: more impact, slight note of popcorn
C: more impact, slightly more nutty and more roasted character
D: more impact, greater roasted note and more nut character
E: more impact, pronounced roasted character.

EXAMPLE 7

A chocolate aroma F is prepared by mixing the following ingredients:

| | | |
|---|---|---|
| isovaleraldehyde | 1% strength solution in ethanol | 1 |
| pheny ethyl alcohol | 0.1% strength in propylene glycol | 1 |
| vanillin | | 5 |
| phenylacetic acid | 1% strength solution in propylene glycol | 5 |
| ethylvanillin | | 50 |
| cocoa powder extract | 30% strength solution in propylene glycol | 948 |
| | parts by weight | 1,000 |

A chocolate aroma G is obtained by adding to F 0.1 part by weight of 2,4(4,6)-dimethyl-6(2)-isopropyl dihydro-1,3,5-dithiazine, a chocolate aroma H is obtained by adding to F 0.1 part by weight of 2,4(4,6)-dimethyl-6(2)-isobutyl-dihydro-1,3,5-dithiazine, a chocolate aroma I is obtained by adding to F 0.1 part by weight of 2,4(4,6)-dimethyl-6(2)-(2-butyl)-dihydro-1,3,5-dithiazine and a chocolate aroma K is obtained by adding to F 0.1 part by weight of 2,4-dimethyltetrahydropyrrolo[2,1-d]-[1,3,5]dithiazine.

F to K are each added in a dosage of 200 ppm to a solution of 5% sucrose in water. A comparison of the flavour of G, H, I and K against F gives the following results:

G: cocoa note is more pronounced
H: chocolate note is more pronounced, somewhat reminiscent of popcorn
I: dark cocoa note is stronger
K: chocolate note is stronger and has a more dusty effect

EXAMPLE 8

A groundnut aroma L is prepared by mixing the following ingredients:

| | |
|---|---|
| 2-methyl-3-ethylpyrazine | 5 |
| phenylacetaldehyde, 10% solution in triazine | 5 |
| 2,5-dimethylpyrazine | 10 |
| groundnut paste | 150 |
| groundnut oil | 830 |
| parts by weight | 1,000 |

A groundnut aroma M is obtained by adding to L 0.2 part by weight of 2,4(4,6)-dimethyl-6(2)-isopropyldihydro-1,3,5-dithiazine, a groundnut aroma N is obtained by adding to L 0.1 part by weight of 2,4(4,6)-dimethyl-6(2)-isobutyl-dihydro-1,3,5-dithiazine, a groundnut aroma 0 is obtained by adding to L 0.1 part by weight of 2,4(4,6)-dimethyl-6(2)-(2-butyl)-dihydro-1,3,5-dithiazine and a ground nut aroma P is obtained by adding to L 0.2 part by weight of 2,4-dimethyltetrahydropyrrolo[2,1-d]-[1,3,5]dithiazine.

L to P are added in a dosage of 500 ppm to milk containing 0.5% of sodium chloride and 0.02% of mono- sodium glutamate. A comparison of the flavour of M, N, O and P against L gives the following results:

M: more impact, typical groundnut character and distinctly stronger roasted character
N: more impact, typical groundnut note and more roasted note O: more impact, typical groundnut note and appreciably stronger roasted note P: more impact, typical groundnut note and more roasted note

EXAMPLE 9

A meat broth Q is obtained by adding to a meat broth 0.3 ppm of 2,4(4,6)-dimethyl-6(2)-isopropyldihydro-1,3,5-dithiazine, a meat broth R is obtained by adding 0.2 ppm of 2,4(4,6)-dimethyl-6(2)-isobutyldihydro-1,3,5-dithiazine, a meat broth S is obtained by adding 0.2 ppm of 2,4(4,6)-dimethyl-6(2)-(2-butyl)-dihydro-1,3,5-dithiazine and a meat broth T is obtained by adding 0.1 ppm of 2,4,dimethyltetrahydropyrrolo-[2,1-d]-[1,3,5]dithiazine.

A comparison of the flavour of Q, R, S and T against the untreated meat broth gives the following results:

Q: the meat broth acquires a fuller and more meaty flavour in the direction of roast meat R: the flavour becomes fuller and more meaty in the direction of roast meat S: the flavour becomes fuller and more meaty T: the flavour becomes fuller and more meaty

What is claimed is:

1. An asymmetrical dihydrodithiazine selected from the group consisting of

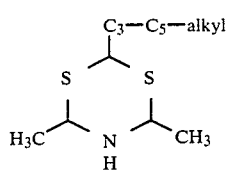

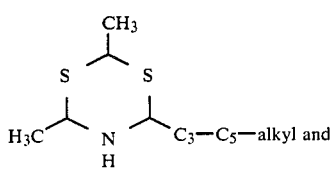

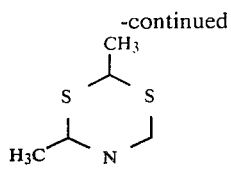

$C_3$—$C_4$—alkylene.

2. A compound according to claim 1 of the formula

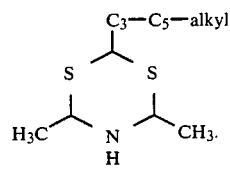

3. A compound according to claim 1 of the formula

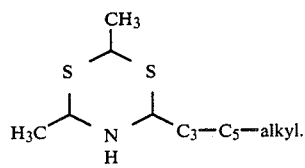

4. A compound according to claim 1 of the formula

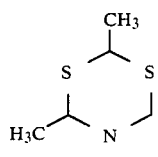

$C_3$-$C_4$—alkylene.

5. A roasting and nut flavoring composition comprising an edible base and a flavoring amount of a compound according to claim 1.

6. A roasting and nut aroma composition comprising an aroma base and an aroma-effective amount of a compound according to claim 1.

7. A process for imparting or enhancing a roasting and nut aroma and flavor to an article or foodstuff which comprises adding thereto an amount effective therefor of a compound according to claim 1.

* * * * *